(12) United States Patent
Pieper et al.

(10) Patent No.: US 8,436,321 B2
(45) Date of Patent: May 7, 2013

(54) OPTICAL BACKGROUND SUPPRESSION SYSTEMS AND METHODS FOR FLUORESCENCE IMAGING

(75) Inventors: Sean B. Pieper, Lincoln, NE (US);
Ahmed Bouzid, Lincoln, NE (US);
Donald T. Lamb, Lincoln, NE (US);
Andrew G. Ragatz, Gretna, NE (US)

(73) Assignee: LI-COR, Inc., Lincoln, NE (US)

( * ) Notice: Subject to any disclaimer, the term of this patent is extended or adjusted under 35 U.S.C. 154(b) by 280 days.

(21) Appl. No.: 12/785,308

(22) Filed: May 21, 2010

(65) Prior Publication Data

US 2011/0284765 A1 Nov. 24, 2011

(51) Int. Cl.
*G01N 21/64* (2006.01)

(52) U.S. Cl.
USPC ..................................... 250/458.1

(58) Field of Classification Search ........... 250/458.1; 356/73, 416
See application file for complete search history.

(56) References Cited

U.S. PATENT DOCUMENTS

| | | | |
|---|---|---|---|
| 6,008,892 A | 12/1999 | Kain et al. | |
| 6,867,851 B2 | 3/2005 | Blumenfeld et al. | |
| 7,286,232 B2 | 10/2007 | Bouzid | |
| 7,464,707 B2 | 12/2008 | Dalgetty et al. | |
| 7,466,418 B2 | 12/2008 | Nilson et al. | |
| 7,474,398 B2 | 1/2009 | Nilson et al. | |
| 7,474,399 B2 | 1/2009 | Nilson et al. | |
| 7,663,664 B2 | 2/2010 | Rice et al. | |
| 7,765,487 B2 | 7/2010 | Cable | |
| 2003/0210465 A1 | 11/2003 | Valenti | |
| 2006/0057708 A1 | 3/2006 | Takamura et al. | |
| 2006/0152726 A1 | 7/2006 | Larsen et al. | |
| 2006/0203244 A1 | 9/2006 | Nilson et al. | |
| 2007/0127118 A1 | 6/2007 | Nilson et al. | |
| 2008/0079802 A1 | 4/2008 | Nilson et al. | |
| 2008/0099020 A1 | 5/2008 | Nelson | |
| 2009/0080194 A1 | 3/2009 | Bouzid et al. | |

FOREIGN PATENT DOCUMENTS

| | | |
|---|---|---|
| JP | 60-207038 A | 10/1985 |
| JP | 7-020037 A | 1/1995 |
| WO | WO 2009/120758 A1 | 10/2009 |

*Primary Examiner* — David Porta
*Assistant Examiner* — Faye Boosalis
(74) *Attorney, Agent, or Firm* — Leydig, Voit & Mayer, LLP; Gerald T. Gray

(57) ABSTRACT

A fluorescence imaging system having an enclosure having an optical excitation and detection system and features designed to suppress or reduce background fluorescence. In certain aspects, all or a portion of the interior walls has a material finish and texture that provides a surface that absorbs at least a portion of any impinging excitation light and which has low auto-fluorescing properties. In certain aspects, a baffle structure is provided on the interior of the structure and is configured to mask portions of the interior and reduce the opening through which light impinges on the detector. In certain aspects, a platform having an optically transparent window is located in the interior of the housing structure for holding a sample for excitation by excitation light from an excitation source, wherein a light-trap structure is positioned or located on an opposite side of the platform relative to the excitation source and configured to receive and contain a substantial portion of any scattered or transmitted excitation light.

25 Claims, 4 Drawing Sheets

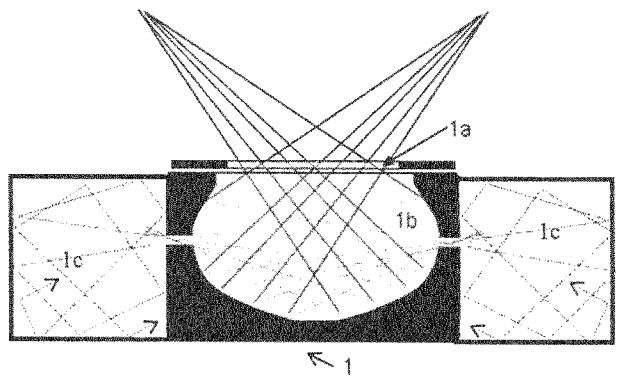

Figure 3a: Low background sample carrier; AR-coated, low auto-fluorescence, transparent window with enclosed light traps behind it.

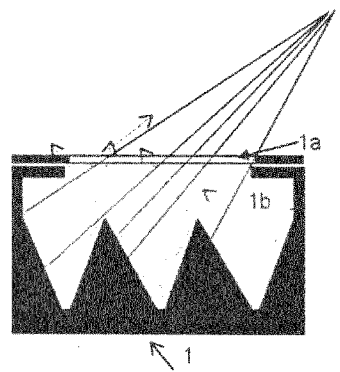

Figure 3b: Low background sample carrier; AR-coated, low auto-fluorescence, transparent window with corrugated low-reflectance surfaces behind it.

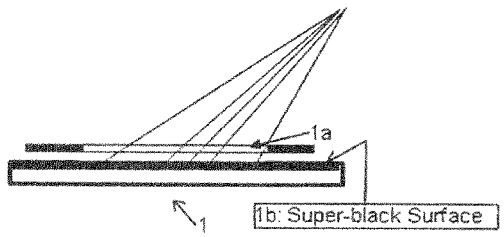

Figure 3c: Low background sample carrier; AR-coated, low auto-fluorescence, transparent window with enclosed light traps behind it.

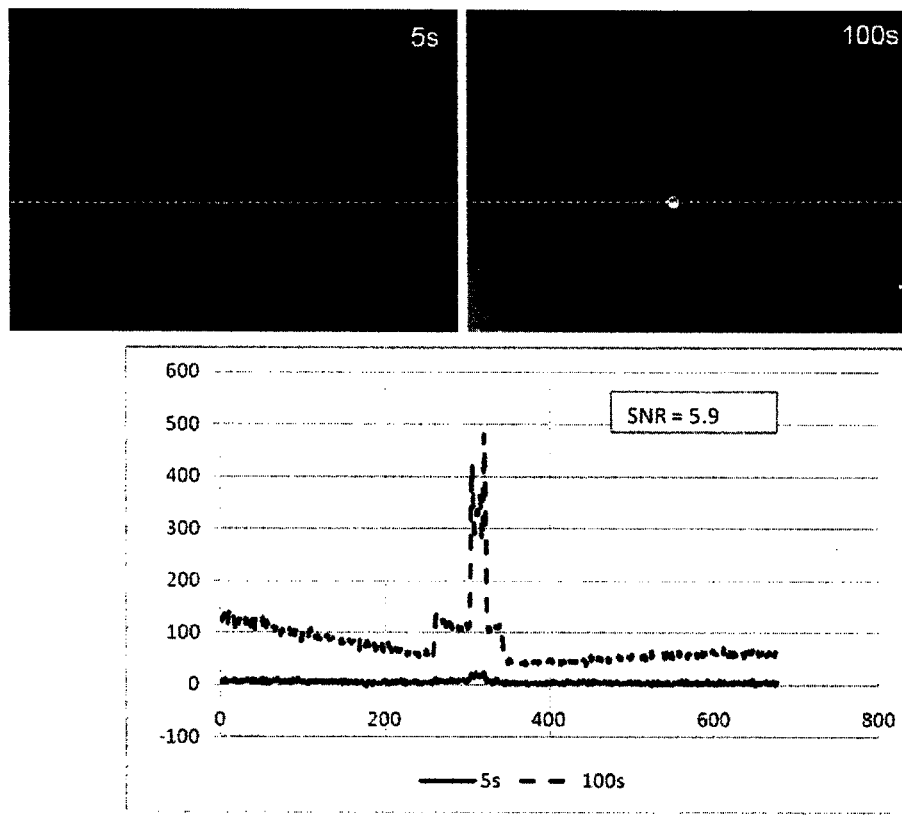
Figure 4: Example of fluorescence imaging performance without the background suppression design of the present invention.

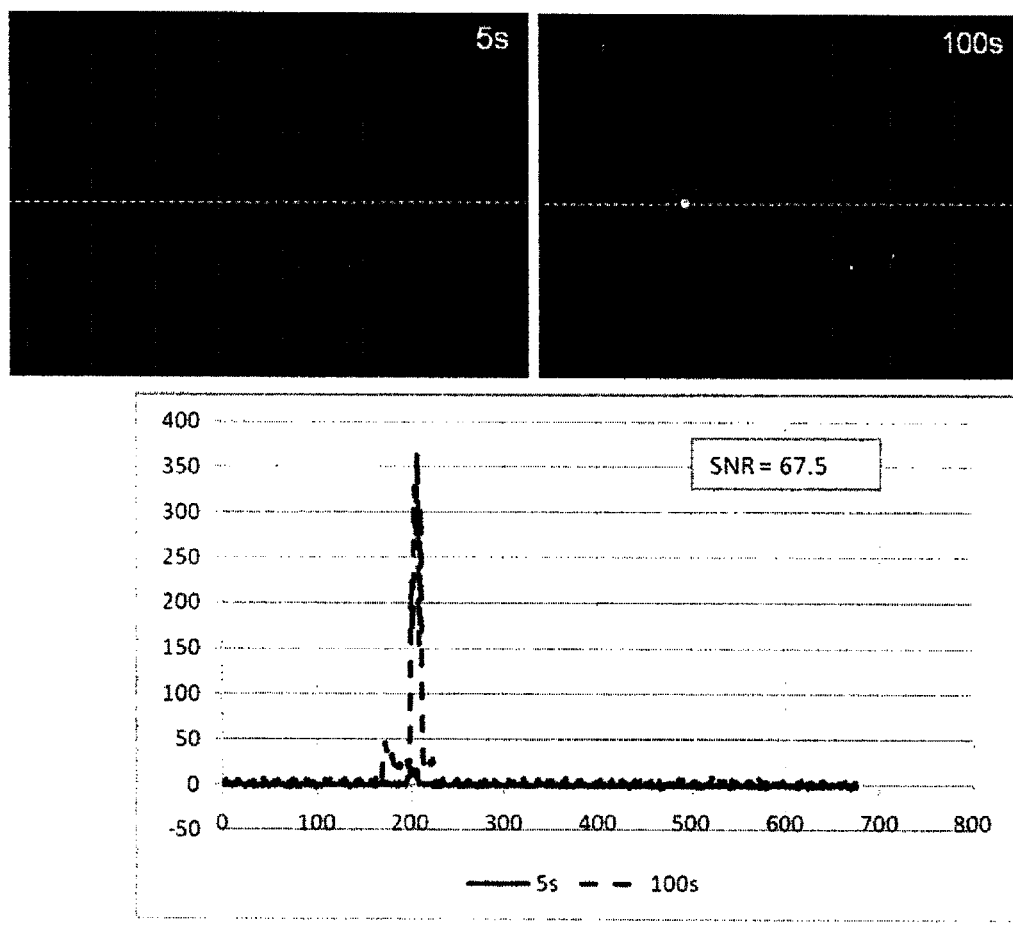
Figure 5: Example of Figure 4 but with optical background suppression.

OPTICAL BACKGROUND SUPPRESSION SYSTEMS AND METHODS FOR FLUORESCENCE IMAGING

CROSS-REFERENCES TO RELATED APPLICATIONS

Not Applicable

BACKGROUND

The present invention relates generally to optical imaging, and more particularly to background noise reduction in fluorescence imaging systems.

Fluorescence imaging typically involves illuminating a fluorescent target with light having wavelength content that matches, at least partially, the absorption spectrum of the fluorescence label and imaging the target with an optical detection system that favors the emitted fluorescence light over any reflected or scattered portion of the excitation light. Like any other detection system, the performance of a fluorescence imaging system can be described by a Signal-to-Noise Ratio (SNR) for a given fluorescence concentration at the target plane. The goal of an optical design is to maximize the fluorescence signal for a given concentration of fluorescence emitting material detected by the imaging system and at the same time minimize its noise level. Elements that contribute to a high SNR for a CCD-based fluorescence imaging system are reflected in the following equation $$SNR = \frac{S}{N} = \frac{S_{Fl}(P, t)}{\sqrt{N_{Dark}^2(t) + N_{Exc}^2(P, t) + N_{AutoFluor}^2(P, t)}}$$

where, $S_{Fl}(P,t)$ is the fluorescence signal from a desired target and varies at low concentrations linearly with the power of the excitation light, P, and CCD exposure time, t, $N_{Dark}^2(t)$ is the dark background signal, i.e. when the excitation light is turned off. $N_{Exc}^2(P,t)$ is the detected optical background signal resulting from excitation light reflected and/or scattered and leaking through the emission filtering system and $N_{AutoFluor}^2(P,t)$ is the detected optical background signal resulting from amounts of excitation light being absorbed by fluorescence-mounting media that itself fluoresces in the passing band of the detection filtering system.

High SNR requires maximizing the detected signal and at the same time minimizing each of the background components. Given an imaging system with efficient light collection and CCD conversion efficiencies, the detected fluorescence signal can be maximized by increasing the light excitation power and/or increasing the exposure time. Equally important, though, is the elimination and/or reduction of the detected background levels that contribute to noise. For CCD-based imaging, $N_{Dark}^2(t)$ consists primarily of two components: read-noise, which does not change as P and t change, and dark-current which does depend on exposure time, t. The former is typically kept low by proper selection of the CCD sensor, the speed of reading out charges from that sensor, and the electronics design around the sensor. The dark-current component is primarily a property of the CCD chip itself and is typically kept under control by properly cooling the CCD. Therefore, $N_{Dark}^2(t)$ is primarily set by the design of the camera part of the detection system and typically sets the minimum level of noise in the system, even if there is no excitation light or fluorescence signals. And, a sensitive system needs to have low $N_{Dark}^2(t)$ to begin with. If, then, the other two components that contribute to noise are completely eliminated, the SNR can be indefinitely increased by increasing P and t. In reality, there will be other limitations, such as photo-bleaching, safety, availability of sources, etc., that limit the increase in P. Even with such limitations, a better design is a design that has no or minimum levels of $N_{Exc}^2(P,t)$ and $N_{AutoFluor}^2(P,t)$.

U.S. Pat. No. 7,286,232 establishes an innovative method for reducing $N_{Exc}^2(P,t)$ significantly in CCD-based wide area imaging. The elements of the patented filtering system were designed to collectively suppress $N_{Exc}^2(P,t)$ to levels much lower than prior art and do so across the whole, relatively large, field of view. It was shown that for the application of imaging mice, which are known to have significant levels of auto-fluorescence, $N_{Exc}^2(P,t)$ was suppressed by the invention well below $N_{AutoFluor}^2(P,t)$ and the resulting noise is then limited by the auto-fluorescence of the target itself, i.e. the mouse.

Imaging in the Near-InfraRed (NIR) wavelength range has recently become the focus of a lot scientific work because of low auto-fluorescence of tissue and other sample-holding media. By reducing the auto-fluorescence of the target itself, demand becomes more stringent on the imaging system itself to not produce optical background levels that can be the limiting factor.

Therefore it is desirable to provide systems and methods that overcome the above and other problems and that allow for maximizing the performance of fluorescence imaging and thus the information that Scientists can use.

BRIEF SUMMARY

The present invention provides systems and methods for reducing background noise in fluorescence imaging systems.

Embodiments of the present invention address, inter cilia, the case where the auto-fluorescence of the target is low. This case corresponds, for example, to imaging western blots on membranes, gels, and glass media. In such cases, the auto-fluorescence from the area around the labeled blots can be low enough, especially in the NIR spectral regime, such that any residual scattering and fluorescence from the imaging system can result in levels of $N_{Exc}^2(P,t)$ and/or $N_{AutoFluor}^2(P,t)$ that limit the sensitivity of the system. Embodiments of the present invention, therefore, assume low dark background, $N_{Dark}^2(t)$, and provides improvements to current filtering technology, and other technologies, to further suppress the optical background in the system, i.e. reducing $(N_{Exc}^2(P,t)+N_{AutoFluor}^2(P,t))$.

According to one aspect of the present invention, a fluorescence imaging system is provided that typically includes a housing structure defining an enclosure and having interior walls defining an interior of the enclosure. The system also typically includes an illumination and detection system having at least one excitation source and a detector configured to detect fluorescent emissions. The system further typically includes a platform located in the interior of the housing structure that is adapted to hold a sample for excitation by excitation light from an excitation source, wherein all or a portion of the interior walls has a material finish and texture that provides a surface that absorbs at least a portion of any impinging excitation light and which has low auto-fluorescing properties.

According to another aspect of the present invention, a fluorescence imaging system is provided that typically includes a housing structure defining an enclosure and having interior walls defining an interior of the enclosure. The system also typically includes an illumination and detection system having at least one excitation source and a detector configured to detect fluorescent emissions. The system further typically includes a platform located in the interior of the housing structure that holds a sample for excitation by excitation light from an excitation source, and a baffle structure located on the interior of the structure and that is configured to mask portions of the interior and reduce the opening through which light impinges on the detector.

According to yet another aspect of the present invention, a fluorescence imaging system is provided that typically includes a housing structure defining an enclosure and having interior walls defining an interior of the enclosure. The system also typically includes an illumination and detection system having at least one excitation source and a detector configured to detect fluorescent emissions. The system further typically includes a platform located in the interior of the housing structure that holds a sample for excitation by excitation light from an excitation source, wherein the platform includes an optically transparent window, and a light-trap structure positioned or located on an opposite side of the platform relative to the excitation source and configured to receive and contain a substantial portion of any scattered or transmitted excitation light.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIGS. 3a, 3b and 3c show embodiments of light trap structures.

FIG. 4 shows an example of fluorescence imaging performance without embodiments of the background suppression design of the present invention.

FIG. 5 shows images and a plot for the same case used in FIG. 4, but with a design that implements embodiments described herein.

DETAILED DESCRIPTION OF THE INVENTION

The present invention provides systems and methods for reducing background noise in fluorescence imaging systems.

As used herein, fluorescence imaging refers to illuminating a target material with excitation light, and where part of that light is absorbed and re-emitted as light with different spectral content, including phosphorescence. Also, fluorescence material or fluorescent material refers to any liquid, solid, or other type of material that absorbs light and re-emits at least a portion of what is absorbed as an optical signal (light) of a different spectral content.

Figure 1:
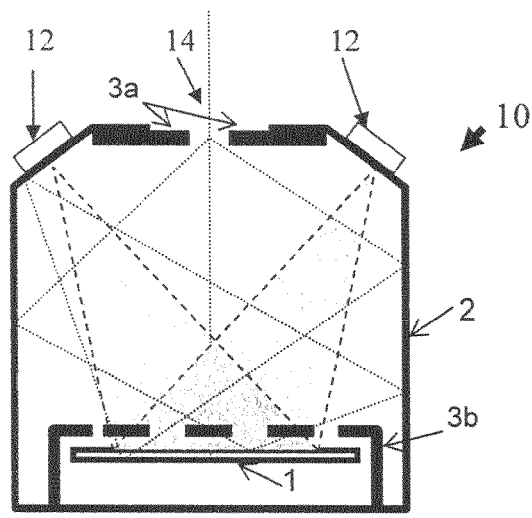
FIG. 1 illustrates a fluorescence imaging system according to one embodiment.
Figure 2:
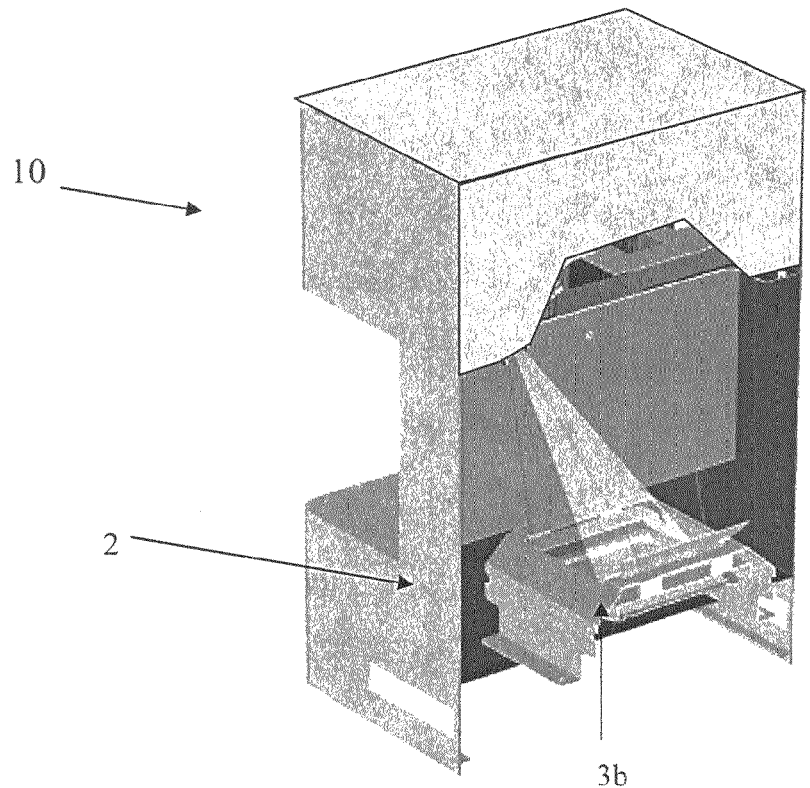
FIG. 2 illustrates a 3-dimensional perspective view of an imaging system according to one embodiment.

FIG. 1 illustrates an imaging system 10 according to one embodiment. FIG. 2 shows a 3-dimensional perspective view of system 10. As shown, system 10 includes a housing structure or enclosure 2 having walls defining an interior and an exterior, for mounting components within the housing structure of system 10. A replaceable panel or drawer opening (not shown) in a wall defines a pathway for receiving a sample for placement on holding plate or platform 1. In certain aspects, holding plate 1 is itself removable. Holding plate 1, in one embodiment, includes or is made of low auto-fluorescing material, textured such that it results in low diffusive reflections from a laser excitation light source or other illumination source as will be discussed in more detail below. In one embodiment, all or a portion of the inside surface of enclosure 2 has a material finish and texture of low reflection and low auto-fluorescence and is configured to keep any scattering and reflections of excitation light enclosed or confined as will be discussed in more detail below. Baffles 3a and 3b, are provided in one embodiment, and are arranged to prevent reflected and scattered light from entering the imaging compartment other than through an entrance aperture (e.g., for an excitation source), and to block any strong reflections from the mounting hardware and automation mechanisms surrounding the target sample and holding plate as will be discussed in more detail below.

Light illuminates the sample/target on sample plate 1 from one or more light sources 12 through one or more aperture(s), and a detector system (not shown) positioned proximal aperture 14 receives light. e.g., emitted fluorescence from the sample/target on sample plate 1.

System 10, in one embodiment, includes an imaging system (not shown). In certain aspects, the imaging system includes one or more excitation sources 12 that provide excitation light, such as one or more laser modules, as well as a detector system (not shown) that includes a camera, CCD, APD or other light detection device(s) or component(s) that receive light via aperture 14. In certain aspects, an excitation source 12 includes a laser, but other sources such as LEDs, arc lamps, white light sources or other sources or devices capable of emitting radiation of a desired wavelength or within a desired wavelength range may be used. A turning mirror is included in certain aspects to provide for scanning of the light source(s) 12 over the sample and/or scanning the field of view of the imaging device over the sample. The imaging system, in certain aspects, includes one or more filters, e.g., a filter wheel, to facilitate filtering the light presented to the imaging device, e.g., to remove undesired wavelengths. In fluorescence detection systems, for example, a filter is useful for removing stray (e.g., reflected) excitation light and/or to allow only light of a specific wavelength range to pass. U.S. Pat. No. 7,286,232, and US Patent Application Publication No. US-2009-0080194-A1, which are hereby incorporated by reference, illustrate examples of useful illumination and detection systems.

In certain embodiments, at least one excitation light source and a detector are provided for fluorescence excitation and detection in the visible through Infra-Red spectral range. For example, in one embodiment, the spectral range is in the near Infra-Red (ex.: from about 670 nm to 1000 nm). In another embodiment, the spectral range is in the visible part of the spectrum 400 nm to 700 nm. Yet, in another embodiment, the spectral range is a combination of both visible and near Infra-Red spectral ranges.

As shown in FIGS. 1 and 2, a sample may be presented to the imaging system on the platform 1 in the interior of the housing structure 2 to allow for illumination and/or excitation by light source(s) 12 and imaging by the imaging device. In the case of fluorescence detection, for example, fluorescent moieties on or in the sample may be excited with one or more laser sources, and the sample may be imaged by the imaging device over a period of time, e.g., seconds or minutes, to determine characteristics of the sample.

In certain aspects, system 10 includes an on-board control system (not shown) to control operation of various internal components, to store data, and/or to interface with external systems such as remote computer systems. For example, the control system in certain aspects includes one or more connectors to external system components such as network connection(s) to remote components or computer systems.

Holding Platform/Plate (1):

According to one embodiment, the sample holding plate 1 includes an opaque, and metal-based or plastic-based (e.g., disposable) material. It is known to one skilled in the art that most materials that absorb light have some form of fluorescence emission and that such behavior is wavelength dependent. Even metal-based material can fluoresce significantly depending on the chemical composition, particularly at the surface layers. Therefore, careful selection of substrate and finish materials for the sample carrier is desirable to ensure that the levels of emitted auto-fluorescence are low in the emission wavelength ranges of interest. According to one embodiment, a material having low auto-fluorescence levels in the near Infra-Red (NIR) wavelength range (650 nm-900 nm) is used. A number of metal-based and plastic based materials were imaged to measure their level of fluorescence emission. Homogeneous, black plastic materials as well as non-oxidized metals were found to have low auto-fluorescence in the NIR wavelength range. Polycarbonate material (Bayer Makrolon 2405-901510) is one material found to have low auto-fluorescence levels in the NIR wavelength range (650 nm-900 nm). One skilled in the art will understand that other types of materials may be used as determined in part by the application (e.g., wavelength range). For example, other useful materials might include black polystyrene or black plated steel.

In certain aspects, low auto-fluorescence can be quantitatively described as a fluorescence emission of less than about 10 photons/nm/second/cm$^2$ in the 800 nm to 900 nm spectral range, or less than about 1000 photons/nm/second/cm$^2$ in the 400 nm to 900 nm spectral range. In general, according to certain aspects, a fluorescent emission of less than about 10,000 photons/nm/second/cm$^2$ provides an improvement over other solutions.

The surface finish of such materials may also reflect the non-absorbed portions of excitation light in varying patterns. For example, a glossy, mirror-like surface finish, even if painted black, reflects a portion of the excitation light mostly in a specular fashion where most of the energy goes in a direction symmetrical to the incident direction. A glossy surface finish can be used to reflect most of the residual light away from the detection system, but is sensitive to polarization and angle of incidence which results in areas brighter than others (glares). A fine structured, rough surface finish, on the other hand, diffuses any residual reflections over a wider range of angles and thus the cumulative reflection patterns are relatively insensitive to polarization and illumination angle. A good finish is a finish that produces a low, diffusive, Lambertian scattering residual pattern. For example, the texture finish #1055-4 from Mold Tech produces a low, diffusive scattering residual pattern. One skilled in the art will understand that other surface finishes may be used as determined in part by the application (e.g., wavelength range). For example, other useful surface finishes might include PM-12 by Protomold or SPI C-1 (Society of the Plastic Industry), or patterns or micro-wells that serve to trap incident excitation light and reflects any residual light in a random, diffusive manner.

According to one embodiment, with reference to FIGS. 3a, 3b and 3c, a transparent optical window 1a in the platform 1 is provided in addition to light-trap cavities or Ultra-Black surfaces behind the window to provide further reduction in scattered excitation and auto-fluorescence. In one embodiment, this is achieved by using an optically transparent window to hold the sample and place light traps or highly absorbing black surfaces behind it (e.g., below the window). In one embodiment, the transparent window is made of low-absorbing, preferably glass (BK7 or Quartz) or optical-quality plastic, e.g., optically transparent plastic material such as PMMA. It should be understood that the optically transparent material may comprise the entire platform 1 or a portion of platform 1. In certain aspects, the window is coated on one or both sides with a low-auto-fluorescence, anti-reflection coating. In certain aspects, the coating is all dielectric. An all-dielectric coating is desirable as it can be much more durable to cleaning needs. Useful dielectrics might include interference-based, all dielectric, anti-reflection coatings which may include magnesium fluoride, silicon dioxide, or tantalum dioxide such as is provided by Chroma Technologies, Omega Optical, Semrock, JDSU, etc. Such coatings can be made to minimize reflections in one or more portions of the optical spectrum that include the wavelengths of the excitation light. They can also be made to minimize reflections over a broader continuous spectrum and include the excitation wavelength(s).

FIGS. 3a and 3b show two embodiments of light traps behind the window 1a. The light trap design shown in FIG. 3a includes a parabolic, low-reflectance, but glossy surface structure 1b to redirect and condense the excitation light that passes through the sample platform window 1a into the enclosed compartment(s) 1c. In another embodiment, the surface structure 1b has an ellipsoid shape or other shape that redirects light as desired. The light trap design shown in FIG. 3b includes corrugated surfaces designed to contain (and absorb) the light (e.g., the light undergoes multiple reflections and upon each reflection a portion of the light is absorbed such that any light ultimately reflected back through window 11b is significantly reduced in magnitude). The structure in certain aspects acts as an optical concentrator and the walls of the corrugations can have a linear cross section as shown, or the walls may have a non-linear cross-section. The inside walls also have low auto-fluorescence, low diffusive reflectance so that light entering inside has minimal chances of escaping and bouncing back into the imaging cavity.

Ultra-Black surfaces, such as surfaces coated with NPL Super Black™, can also be placed behind the window as shown in FIG. 3c. NPL Super Black was shown to absorb 99.7% of incident light, better than gold black and black paint. In one embodiment, enhanced absorption is obtained through a finely controlled etching procedure to produce a unique morphology having micro-well structures that are tens of microns deep which trap any light incident on it. The process can be applied to different materials and thus can be made of low auto-fluorescing surfaces. The surfaces of the light trap structures shown in FIG. 3 may be coated or painted with NPL Super Black, as may be the interior surfaces of the housing structure and other components interior to the device.

Enclosure (2):

According to one embodiment, the enclosure is made of low auto-fluorescing, opaque plastic or metal. It is preferred that the inside surface be non-glossy and painted, anodized, or otherwise finished with low auto-fluorescing material. Since information about fluorescing properties of finish materials is rarely known or provided by material suppliers, it is important to use sensitive fluorescence detection systems, such as LI-COR's Odyssey® to measure the amount of fluorescence emitted. Even materials of similar color, like a black color, can have significantly different fluorescence properties. For example, some black paints were found to have low fluorescence and phosphorescence in the NIR as needed in one embodiment. One useful material is conductive baking enamel #8100-ELIK paint, which was found to be of low auto-fluorescing properties. Other useful materials might include black polycarbonate, black polystyrene, or black plated steel.

Baffles (3a and 3b):

According to one embodiment, baffles internal to the enclosure are provided to i) mask any hardware that may need to be placed inside the enclosure and cannot easily be made such that it does not reflect excitation light or emit some fluorescence, and ii) limit the opening that desired fluorescence light needs to enter the imaging compartment from. Preferably, also, this stray light control is done with baffle shapes that help diffuse/direct any residual reflections over large areas and thus avoid localized, hot spots in any residual background level. In certain aspects, the baffles are made of sheet-metal or plastic with the same material, paint, and finish as the enclosure. The baffles may of course be made of materials different from the enclosure.

Test Results with Embodiments Described Above:

FIG. 4 shows an example of fluorescence imaging performance without embodiments of the background suppression design of the present invention. The sample consists of a low concentration IRDye® 800CW dye. FIG. 4 shows two images and one plot. Both images were taken with a system of similar form as in FIG. 1, but with a tray plate and enclosure design different from those described above and with no baffles. This instrument was designed for imaging small animals which typically have much higher tissue scattering and auto-fluorescence levels than the levels from the tray and enclosure of the instrument itself. So, no particular effort to suppress the latter was needed. But, if the same instrument were to be used with targets that have lower scattering/auto-fluorescence levels than mice, where longer exposures and/or more laser power are needed, the residual levels from the instrument itself become the limit. This can be shown by comparing 5 s and 100 s exposure times, for example. As the images and the plot in FIG. 4 show, increasing exposure from 5 s to 100 s reveals that the detected optical background levels limit the performance, which thus becomes un-acceptable.

FIG. 5 shows images and a plot for the same case used in FIG. 4, but with a design that implements embodiments described herein. It is clear that the optical background contribution from the instrument is reduced significantly to levels that easily allow for exposures much more than 100 s without any residual optical background become a limiting factor again. In the example shown, SNR increased by ~11.5× when increasing the exposure time from 5 s to 100 s (20×). This indicates that the contribution to noise from the residual optical background is minimal. Tests were also conducted with the new design to show that up-to 10 min of exposure, only minimal levels of optical background can be detected with embodiments of the invention.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A fluorescence imaging system, comprising:
a housing structure defining an enclosure and having interior walls defining an interior of the enclosure;
an illumination and detection system having at least one excitation source and a detector configured to detect fluorescent emissions;
a platform located in the interior of the housing structure and adapted to hold a sample for excitation by excitation light from an excitation source,
wherein all or a portion of the interior walls has a material finish and texture that provides a surface that absorbs at least a portion of any impinging excitation light and which has low auto-fluorescing properties.

2. The imaging system of claim 1, wherein the material finish includes a low-auto-fluorescing paint.

3. The imaging system of claim 2, wherein the paint includes a black conductive baking enamel paint.

4. The imaging system of claim 1, wherein the platform includes an opaque metal or plastic material.

5. The imaging system of claim 4, wherein the material includes a polycarbonate material.

6. The imaging system of claim 4, wherein the platform includes a textured surface finish.

7. The imaging system of claim 6, wherein the platform has a rough surface finish that produces a diffusive scattering pattern for any impinging excitation light.

8. The imaging system of claim 6, wherein the surface finish produces a Lambertian scattering profile for any impinging excitation light.

9. The imaging system of claim 1, wherein the platform includes an optically transparent window.

10. The imaging system of claim 9, wherein the window comprises glass or optically transparent plastic.

11. The imaging system of claim 10, wherein at least one side of the window is coated with a dielectric anti-reflection coating.

12. The imaging system of claim 9, further including a light-trap structure positioned on an opposite side of the platform relative to the excitation source and configured to receive and contain a substantial portion of any scattered or transmitted excitation light.

13. The imaging system of claim 12, wherein the light trap structure includes a parabolic or ellipsoid shaped cavity.

14. The imaging system of claim 12, wherein the light trap structure includes a plurality of corrugated surfaces or micro wells.

15. The imaging system of claim 12, wherein the light trap structure includes a surface coated with a black conductive baking enamel paint.

16. The imaging system of claim 9, further including a baffle structure located on the interior of the structure and configured to mask portions of the interior and reduce the opening through which light impinges on the detector.

17. A fluorescence imaging system, comprising:
a housing structure defining an enclosure and having interior walls defining an interior of the enclosure;
an illumination and detection system having at least one excitation source and a detector configured to detect fluorescent emissions;
a platform located in the interior of the housing structure and adapted to hold a sample for excitation by excitation light from an excitation source, and
a baffle structure located on the interior of the structure and configured to mask portions of the interior and reduce the opening through which light impinges on the detector,
wherein all or a portion of the interior walls has a material finish and texture that Provides a surface that absorbs at least a portion of any impinging excitation light and which has low auto- fluorescing properties.

18. The imaging system of claim 17, wherein the platform includes an optically transparent window and wherein the imaging system further includes a light-trap structure positioned on an opposite side of the platform relative to the excitation source and configured to receive and contain a substantial portion of any scattered excitation light.

19. A fluorescence imaging system, comprising:
- a housing structure defining an enclosure and having interior walls defining an interior of the enclosure;
- an illumination and detection system having at least one excitation source and a detector configured to detect fluorescent emissions;
- a platform located in the interior of the housing structure and adapted to hold a sample for excitation by excitation light from an excitation source, wherein the platform includes an optically transparent window; and
- a light-trap structure positioned on an opposite side of the platform relative to the excitation source and configured to receive and contain a substantial portion of any scattered or transmitted excitation light,
- wherein all or a portion of the interior walls has a material finish and texture that provides a surface that absorbs at least a portion of any impinging excitation light and which has low auto-fluorescing properties.

20. The imaging system of claim 19, wherein the light trap structure includes a parabolic or ellipsoid shaped cavity.

21. The imaging system of claim 19, wherein the light trap structure includes a plurality of corrugated surfaces or micro wells.

22. The imaging system of claim 19, wherein the light trap structure includes a surface coated with a black conductive baking enamel paint.

23. The imaging system of claim 19, wherein the window comprises glass or optically transparent plastic.

24. The imaging system of claim 23, wherein at least one side of the window is coated with a dielectric anti-reflection coating.

25. The imaging system of claim 23, wherein the window comprises PMMA.

* * * * *